United States Patent [19]
Vogelsong et al.

[11] Patent Number: 5,818,900
[45] Date of Patent: Oct. 6, 1998

[54] IMAGE SPOT NOISE REDUCTION EMPLOYING RANK ORDER

[75] Inventors: Thomas L. Vogelsong, Jamesville, N.Y.; William John Dallas, Tucson, Ariz.; Hans Roehrig, Tucson, Ariz.; Eugene J. Gross, Tucson, Ariz.

[73] Assignee: Infimed, Inc., Liverpool, N.Y.

[21] Appl. No.: 806,067

[22] Filed: Feb. 25, 1997

[51] Int. Cl.⁶ .................................................. G01N 23/04
[52] U.S. Cl. ......................... 378/62; 378/98; 250/370.09
[58] Field of Search ............................. 378/62, 98, 98.4; 250/370.09, 370.11

[56] References Cited

U.S. PATENT DOCUMENTS

| | | | |
|---|---|---|---|
| 4,995,068 | 2/1991 | Chou et al. | 378/189 |
| 5,434,418 | 7/1995 | Schick | 250/370.11 |
| 5,708,693 | 1/1998 | Aach et al. | 378/62 |

*Primary Examiner*—David P. Porta
*Assistant Examiner*—David Vernon Bruce
*Attorney, Agent, or Firm*—Trapani & Molldrem

[57] ABSTRACT

An x-ray or gamma ray image that is produced as an array of pixels is treated for reduction or elimination of white spot noise. Two or more successive images in registry are produced and the pixel values at each pixel location are inspected for the respective images. The pixel values are considered according to rank, e.g. from dark to bright, and the lowest ranking pixel value is selected for each pixel location. This creates an output image that is substantially free of the spot noise that results from direct impingement of the x-ray photons on the imaging device. This technique is especially useful in portal imaging for radiation therapy, dental imaging, or industrial imaging.

7 Claims, 8 Drawing Sheets

IMAGE SPOT NOISE REDUCTION EMPLOYING RANK ORDER

BACKGROUND OF THE INVENTION

This invention relates to techniques for enhancing the quality of video images, and is more particularly concerned with techniques for minimizing or eliminating spot noise that can occur in x-ray imaging. The invention is more particularly concerned with a technique that enhances image quality in a simple and straightforward fashion without increasing exposure to the patient.

In certain types of x-ray detection and imaging, a spotting problem can arise from the incidence of x-rays on the detection medium. In certain types of detectors, namely those employing CCDs, CIDs, or other solid-state imaging devices, photons of radiation that directly impact the detecting medium can cause high levels of signal within that pixel, which produce artifacts in the radiological image, that is, bright spots that do not represent structure in the actual object being x-rayed. This limits the applicability of such detectors in a number of applications, both medical and industrial.

The typical solid-state x-ray imaging detector array uses a two-step process to create the video image. First, the x-ray photons strike a conversion layer that converts the x-ray radiation to a visible light output, and then the visible light falls on a light sensing array, e.g., a CCD. A step can also be taken to keep the x-ray radiation from interacting directly with the light sensing array. For example, the conversion layer can be constructed to absorb the x-ray radiation, or alternatively there can be a layer of a radiosorptive material, e.g., leaded glass, interposed between the conversion layer and the light sensing array. This material is intended to pass light in the visible spectrum, but to absorb the x-ray photons. Ideally, the light sensing array is designed to react photoelectrically only to light in a specific wavelength band, e.g., only to green light (about 560 nm), with the x-ray photons passing through without generating any electrons or holes. However, in reality some portion of the x-ray photons that are incident on the sensor will create a signal on the light sensing array. Because the x-ray photon has a much higher energy than that of a visible light photon, the picture element or pixel involved will become flooded, i.e., will appear as a white spot at that location on the image.

Current techniques to avoid direct x-ray photon interactions on the imaging sensor have not been entirely successful, and consequently these images so-produced characteristically contain white spot noise, e.g., artifacts that appear as grains of salt on the image. These spots degrade the image.

White spot noise can also occur in many x-ray imaging applications. One such application is portal imaging, where a solid-state sensor is employed. In portal imaging (used for positioning patients in radiation therapy and monitoring the regions of the anatomy that are irradiated), a scintillator plate is optically coupled to a solid state imaging array, such as a charge coupled device or CCD. While the CCD is designed to be out of direct line with the x-ray generator, scattered x-ray photons can directly impinge on the detector, causing white spots. The scintillator plate can be directly or optically coupled to the solid state sensor. The overlying scintillator does not block all the x-ray photons. Some fraction will penetrate into the CCD device, and create white spot noise. Another example is that of the sensor in which the scintillator is fiber-optically coupled, or lens coupled, to one or a multiple of CCDs for use in radiology imaging. In this case as well, x-ray leakage or scattered radiation may strike the CCD detector, causing white spots. In these and other similar applications, including industrial x-ray inspection, motion is or can be limited, permitting the imaging sensor to produce a sequence of images taken in registry. However, each of the images in a given sequence is likely to have spot noise, although the spots will occur at random locations that vary from exposure to exposure.

An example of a portal imaging arrangement is described in Chou et al. U.S. Pat. No. 4,995,068, entitled Radiation Therapy Imaging Apparatus. An example of a solid-state intraoral radiology imager, e.g., as used in dental imaging, is described in Schick U.S. Pat. No. 5,434,418, entitled Intra-Oral Sensor for Computer Aided Radiography. While these two references describe some of the many possible applications, neither of them addresses the white-spot noise problem as discussed just above.

In those detectors where white spots are a problem, means are usually employed to reduce the likelihood of unwanted x-ray photons striking the detector. One approach has been to add shielding in the form of lead or other high-Z material to block scattered radiation. Shielding of this sort can typically be employed in applications where the image light path is altered through the use of mirrors. In such applications, the shielding can be positioned along or across the line-of-sight path between the x-ray generator and the solid state detector. Another approach, especially for lower-energy applications, has been to employ an x-ray absorbent, optically transparent layer between the scintillator and the solid-state detector. This can include a lead-doped fiber in a fiber optic coupler or lead-doped glass in lenses. It is also possible to employ photodetector arrays which are less sensitive to the x-ray photons. However, such sensors are typically quite expensive. These are also often less sensitive to the visible radiation produced by the scintillator, which thus requires increasing patient exposure to compensate.

OBJECTS AND SUMMARY OF THE INVENTION

Accordingly, it is an object of this invention to provide a technique to minimize or eliminate the spot noise described above and to avoid the drawbacks of the prior art.

It is another object to provide a technique that can be employed in a system using a standard scintillator and a standard image sensor array.

It is a further object to provide a spot noise elimination technique which is straightforward and does not significantly increase equipment or exposure burdens.

The concept of this invention can be employed with standard scintillators, such as Gadolinium Oxysulfide, Cesium Iodide, Thallium-doped Cesium Iodide, or other available material. The photosensor array can be a standard device as well, such as a CCD or a CID. In a device of this type, an image is acquired by integrating a photoelectric signal over some integration period T. This period can be divided or segmented into N multiple successive frames each of a shorter period T/N. For example, the imaging array could integrate for a time T/4, then read out and store image #1, integrate for a second time T/4, read out and store image #2, integrate for time T/4, read out and store image #3, and then integrate for time T/4, read out and store image #4. The total integration time is still T. Because the images 1, 2, 3, and 4 are taken in quick succession, they can be easily acquired in registry with one another.

The imaging array is arranged to capture the image as a grid of picture elements or pixels. The grid is generally an array of n lines, with each line containing m pixels. Each pixel thus has a given pixel location (M,N) where N and M have any integral value from 0 to n−1 and 0 to m−1, respectively. The number of pixels depend on the desired resolution. For example, the grid may be an array of 512 by 512, with pixel locations from (0,0) to (511, 511).

It has been observed that the x-ray hits (which cause the spot noise described above) are random events. The x-ray hits may occur at any given pixel location in any given frame. Because of the randomness of this phenomenon, it is statistically unlikely that an x-ray hit will occur at the same pixel location in each of two successive frames. It is even more unlikely that an x-ray hit will occur at the same pixel location in N out of N frames, for a number N more than two.

Because the video signal is stored and recorded as a signal strength, or brightness value, for each of the (n×m) pixel locations, it is possible to examine the various image frames pixel by pixel, and examine each pixel in each of the several frames. The respective pixel values can be ranked from highest to lowest, in terms of brightness value. A rank order filter technique is employed to select a certain place in the ranking for the pixel values at each pixel location. For white spot noise elimination, the best selection is to pick the minimum value of the set of frames, and assemble a resulting image based on the selected lowest value pixel for all of the pixel locations. Because of the randomness of the white spot noise, and the order that is inherent in the image, the resulting output image will be substantially free of white spot noise. Even where there are a large number of white spots in the raw image, the white spots are greatly reduced where the filtering selects the lower ranking pixel in two frames (N=2), and are virtually eliminated where the filtering selects the lowest ranking pixels in three frames (N=3). This filtering eliminates the white spot noise without degradation and without loss of sharpness in the underlying image.

The image processing or filtering can be carried out in any convenient computer or digital signal processor. In one possible embodiment, the two, three or four (or more) images in registry are acquired and stored digitally. Then, the values from the first pixel for all four images are compared, and the minimum (or other selected rank) value is stored in the first pixel location of an output image. All remaining pixels are processed in like manner, thus yielding the output image. Another possible embodiment, which requires less storage and less latency, is to bring the first image into a frame buffer as it is acquired. Then, as the second image is acquired, the pixel values of the incoming second image are compared to the values of the stored (first) image. The minimum of the two values is placed back into the frame buffer at that pixel location. After the second image is complete, the frame buffer contains the minimum value (pixel-by-pixel) image of the two frames. As a third (and subsequent) image is acquired, the pixel values are compared pixel by pixel with the stored image. If the incoming pixel value is smaller, the smaller value is placed into the frame buffer at that pixel location. This sequence continues until the last of the N images is acquired. The frame store then holds the minimum (pixel by pixel) image over the acquired frames.

As mentioned before, the pixel value that is selected need not be that of lowest rank or value. For some applications, it may be desirable to select the pixel of highest rank, or of an intermediate rank. This technique can be used for eliminating or reducing blemishes or artifacts that occur for other reasons, and should not be considered limited only to the white spot noise problem discussed above.

The above and many other objects, features, and advantages of this invention will become apparent from the ensuing detailed description of a preferred embodiment, which should be read in conjunction with the accompanying Drawing.

DETAILED DESCRIPTION OF THE PREFERRED EMBODIMENTS

Figure 1:
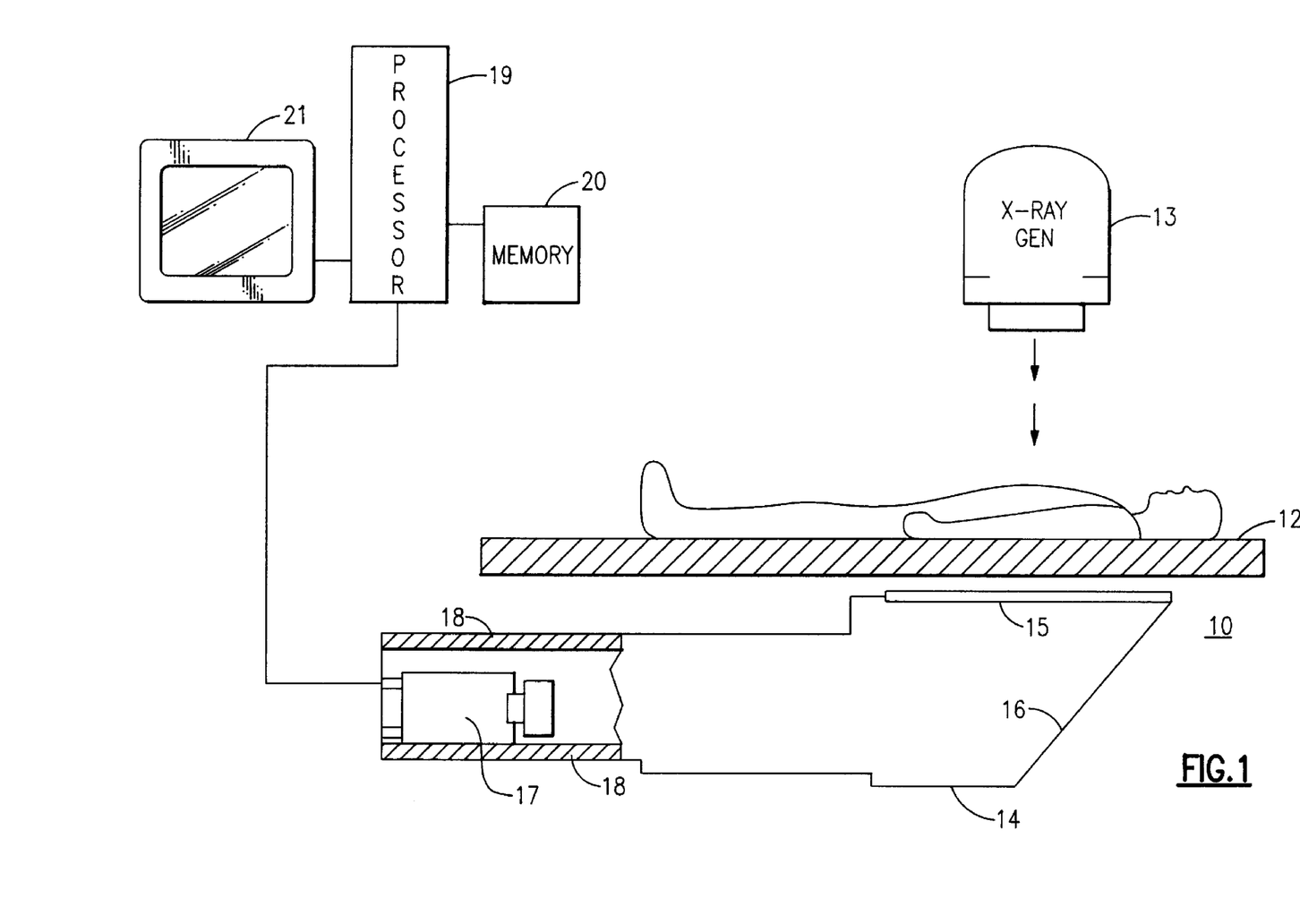
FIG. 1 is a schematic view showing a portal imager for use with a therapeutic x-ray arrangement, for explaining the process of the present invention.

With reference now to the Drawing, FIG. 1 illustrates a portal imaging arrangement to which the rank-order filter process of this invention can favorably be applied. As mentioned before, rank-order filtering can be used with many other applications, such as portal imaging, but intraoral radiology provides a convenient example.

In FIG. 1, a radiation therapy imager 10 is provided as generally described in Chou et al. U.S. Pat. No. 4,995,068. A patient is positioned on a table 12 and an x-ray generator 13 is positioned to expose the patient to radiation, e.g., as a part of an oncology treatment. Below the table 12 an elongated light box 14 has an imaging plate 15 aligned with the patient and with the x-ray generator 13 to produce a visible light image. A mirror 16 reflects this image to a camera 17 at the distal end of the light box. As shown here, some lead shielding 18 is provided in the vicinity of the camera 17 to absorb stray x-ray photons. However, some x-ray radiation will scatter, and can still reach the solid state imager within the camera. This can produce spot noise, which is to be described shortly. Also shown here are an image processor 19 with an associated image memory device 20, and a video display unit 21 for presenting the image of the video picture.

Figure 2:
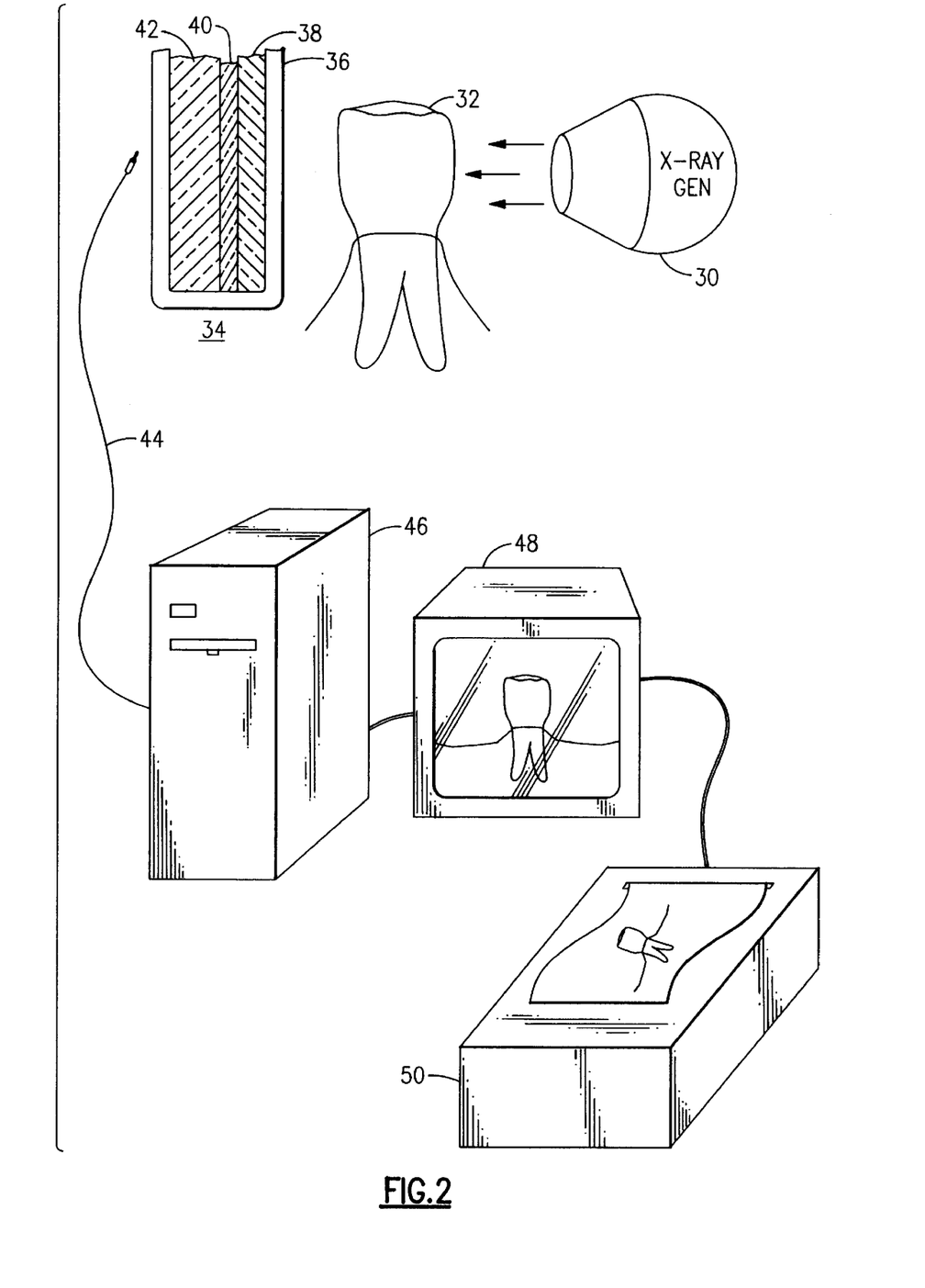
FIG. 2 is a schematic view showing a dental x-ray arrangement with an intraoral x-ray sensor, also for explaining the process of the present invention.
Figure 3:
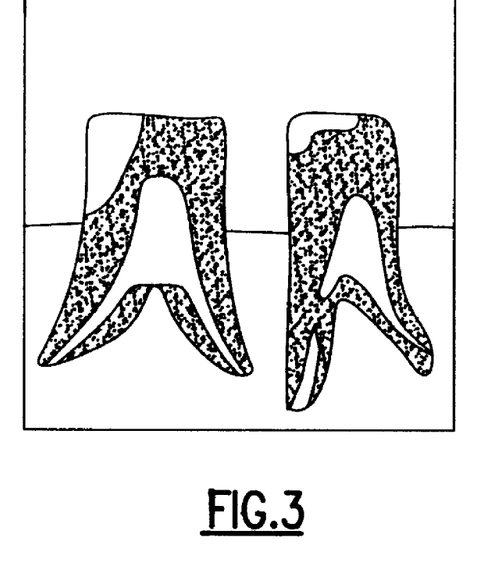
FIG. 3 is an example of a dental radiogram.
Figure 4:
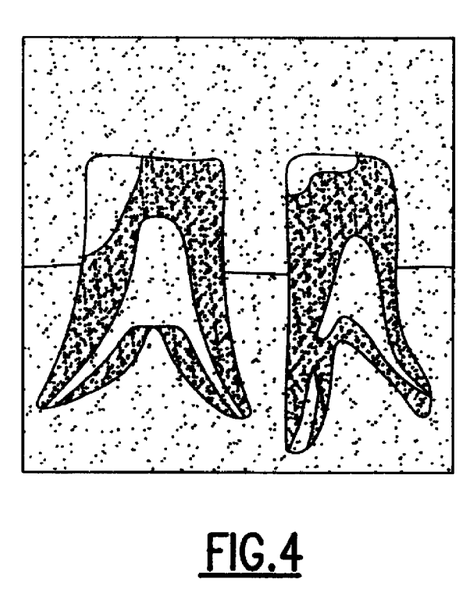
FIG. 4 shows the dental radiogram of FIG. 3 with the white spot noise problem to which this invention is addressed.

Shown in FIG. 2 is an oral imaging arrangement, in which a dental x-ray generator 30 projects low-energy x-ray radiation towards an object 32, which here can be a dental patient's tooth. An intraoral x-ray imaging sensor 34 is positioned within the patient's mouth to pick up the x-ray image of the target 32. This sensor 34 can be of the type described generally in Schick U.S. Pat. No. 5,434,418, although other sensor designs are possible. The sensor 34 contains, within an envelope or sheath 36, a radio-luminescent screen 38, e.g., a conversion layer of thallium-doped cesium iodide or another suitable material. This screen or conversion layer 38 converts x-ray photons into a longer wavelength, e.g., visible light. This layer 38 is separated by a transparent glass layer 40 from a video pickup device 42, such as a CCD. The glass layer 40 can be lead doped so as to pass the visible light but block stray x-ray radiation. The CCD 42 is sensitive to the wavelengths generated by the radioluminescent screen 38, but does not interact significantly with the x-ray photons produced by the generator 30. The image captured on the CCD device 42 can be carried by a video cable 44 to a computer device 46. The latter processes the image and presents it on a video display 48 or produces a paper or film copy on a printer 50. An example of the radiograph image that is produced could appear, e.g., as shown in FIG. 3. Here, the appearance of the image is reversed, so that the denser areas (such as silver fillings) appear as white areas. The various tissues in the target 32 create good contrast in the final image. Unfortunately, because the energy of the x-ray photons is rather high compared with visible light, and because the sensor 34 is in a direct line of sight with the x-ray generator 30, there is a finite probability that the x-ray photons will interact with at least some of the picture elements or pixels in the CCD device 42. When the x-ray photon passes through the target 32, conversion layer 34 and the leaded glass 40, and strikes a pixel of the device 42 but does not pass entirely through the CCD device 42, the CCD will produce a bright light signal, i.e., a white spot, at that given pixel. This is a random phenomenon, and for a given image, this creates the appearance of numerous small bright spots at random locations, such as grains of salt, as shown in FIG. 4. In this example, because of the image reversal used for paper or white backgrounds, the spot noise creates the appearance of dark or black spots or splotches. In a non-reversal image, the spot noise would appear as white spots or blotches. In either event, the spots interfere with contrast and resolution of the image.

Figure 5:
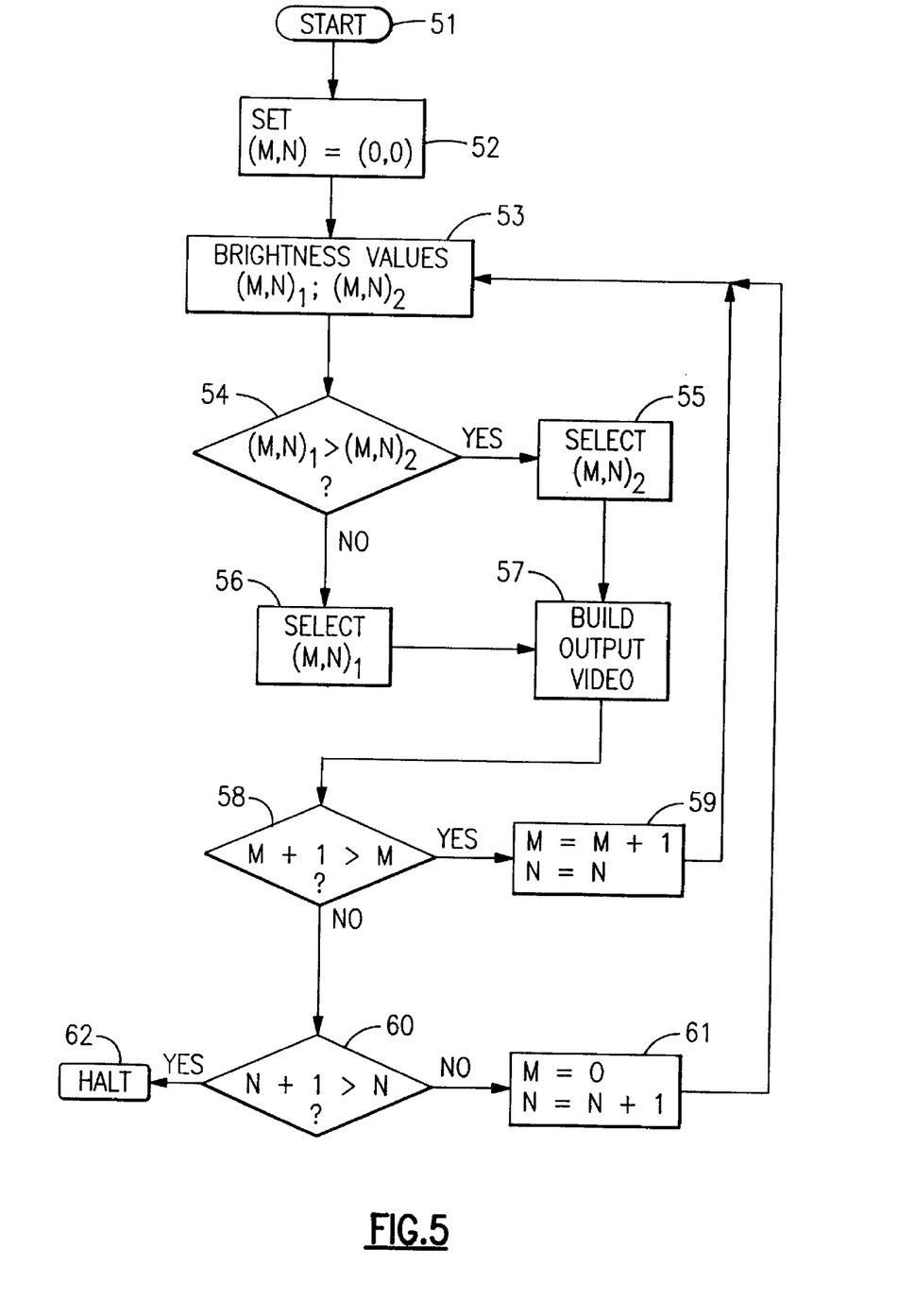
FIG. 5 is a flow chart for explaining the rank order filtering process of this invention.

The rank-order filtering process can be explained with reference to the flow chart of FIG. 5. This process can be carried out using the memory and processing capability of the processor 19 or the computer 46. As described above, two successive images can be captured by the portal imager 10 or the intraoral sensor 44 and the images stored as respective sequences of pixels. Because there is no movement of the object 32 between images, the two images are in registry with one another. Here, the images are configured as a grid of n rows or lines, with m pixels in each row, so each image is stored as an array of (n×m) pixels stored in respective n×m memory locations. Each pixel can be considered as having a pixel location of (M,N) where M and N are values for pixel number and row number between 0 and m−1 or n−1, respectively.

Once the two images have been captured and stored in memory, the rank order filtering process is started [block 51], and a counter sets the pixel number initially at (M,N)= (0,0) [block 52]. Brightness or luminance values of the respective pixels at the same locations, i.e., $(M,N)_1$ and $(M,N)_2$, are compared for both images [block 53]. If the brightness value of the second pixel $(M,N)_2$ is higher than that of the first pixel $(M,N)_1$ [block 54] then the first pixel $(M,N)_1$ is selected [block 55]. Otherwise, the second pixel $(M,N)_2$ is selected [block 56]. The selected pixels, which in each case will be the lower ranking pixels in terms of brightness, are assembled in another memory location [block 57]. The horizontal pixel location number M is compared with the maximum number m−1 [block 58]. If the end of the row has not been reached (i.e., pixel number is less than m−1), the pixel number M is advanced to M+1 [block 59]. When the end of the row is reached the pixel row number N is checked against the maximum row number n−1 [block 60]. As long as the row number is within a valid range, the process goes to the next row number N+1 at the beginning of the row (M=0) [block 61]. The program will halt after the last pixel in the final row [block 62]. At that point, the resulting filtered video image can be used as an output image with substantially all of the spot noise eliminated.

Figure 6:
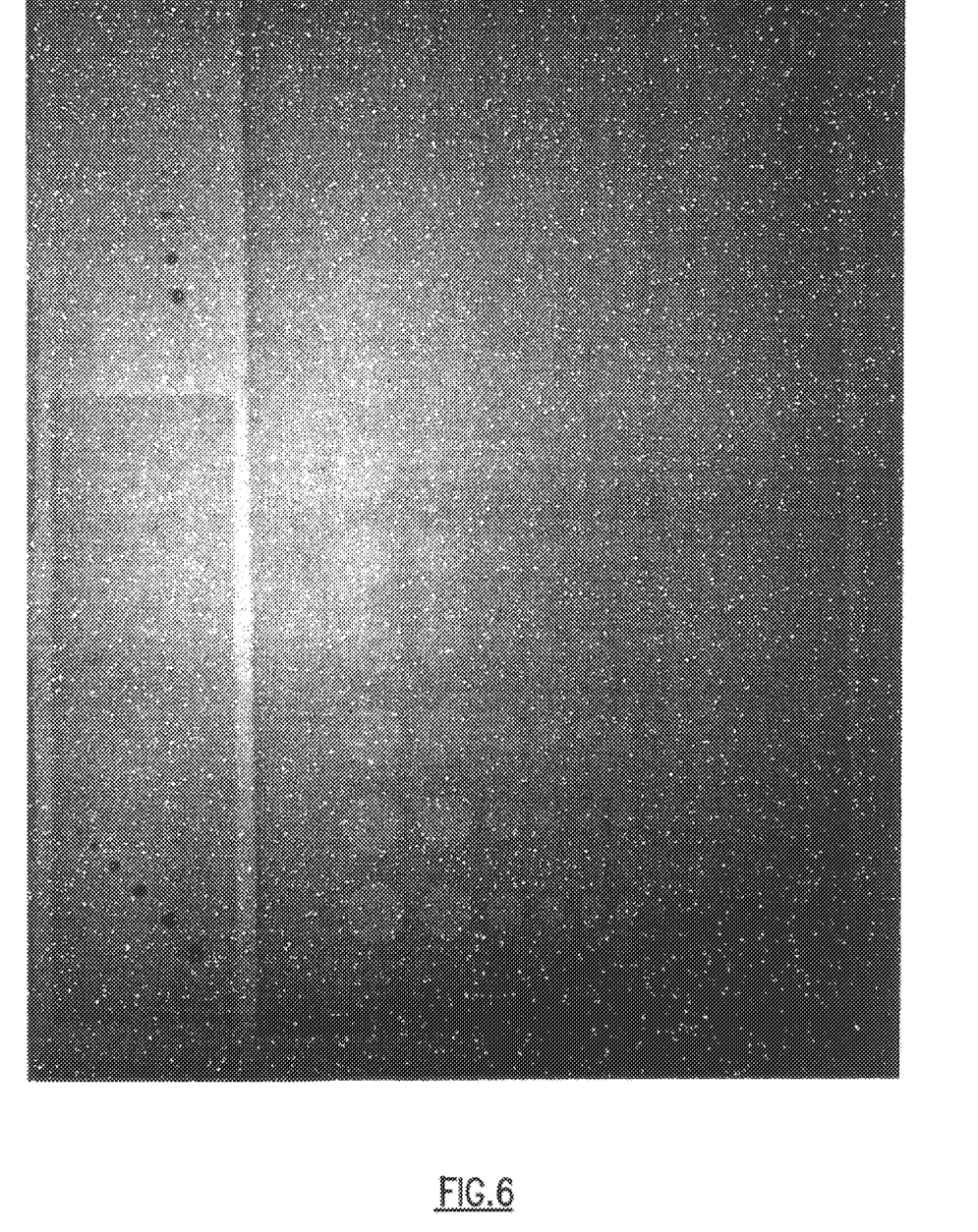
FIG. 6 illustrates an example of a raw image of a calibration target, showing white spot noise.

A raw image of a standard portal imaging target is shown in FIG. 6, in which there is an abundance of white spot noise appearing as grains of salt at random locations over the entire image. The detail in this image is severely clouded by this white spot noise.

Figure 7:
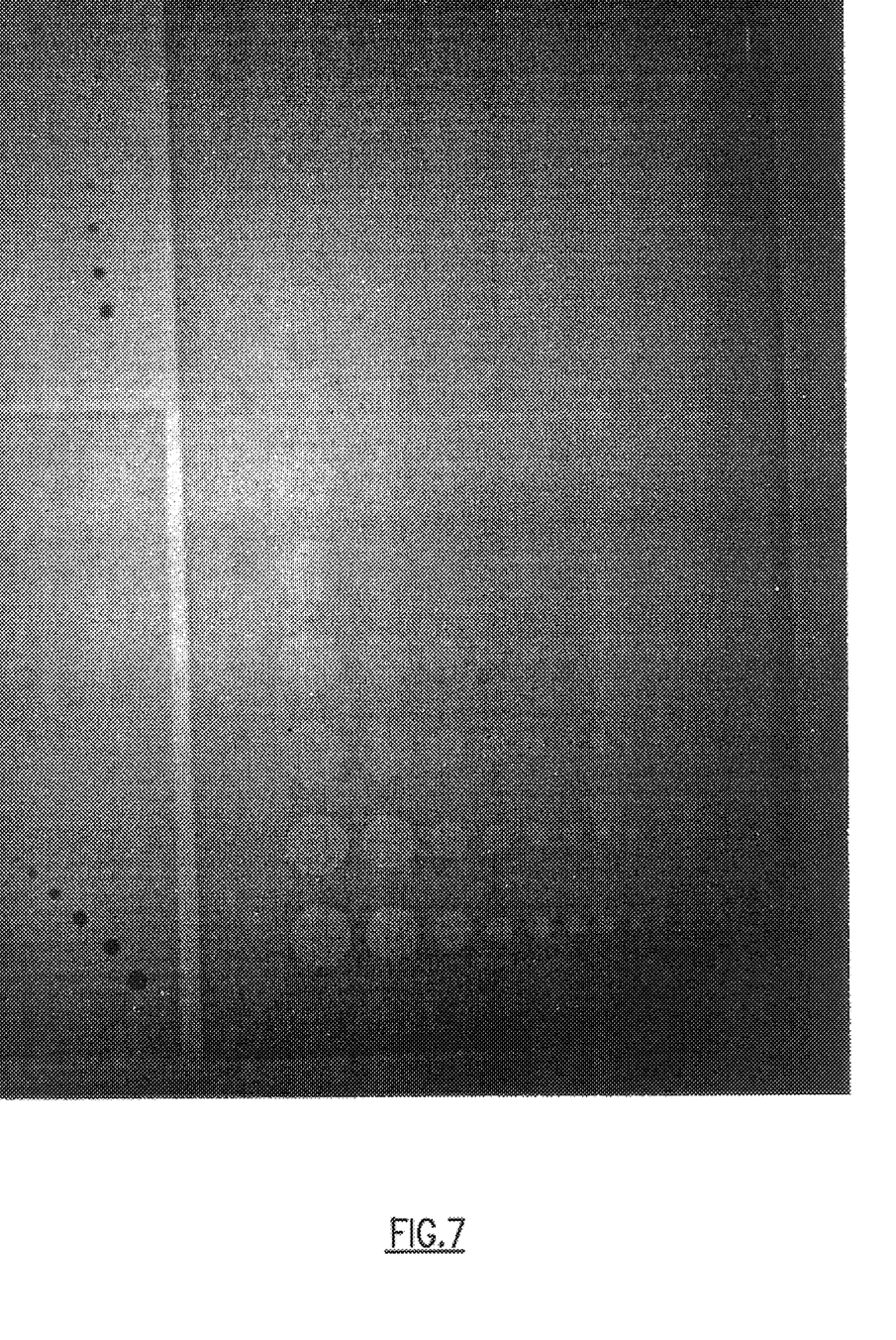
FIGS. 7, 8 and 9 illustrate examples of the image of FIG. 6 processed using rank-order filtering for elimination of white spot noise.

FIG. 7 shows a filtered image in which the lower ranking pixels of two successive images were selected for the output image (MIN-2). Because of the randomness of the white spot problem, most of the white spots are removed by the rank order filtering process, and only a few white spots remain. The contrast and resolution are greatly improved.

Figure 8:
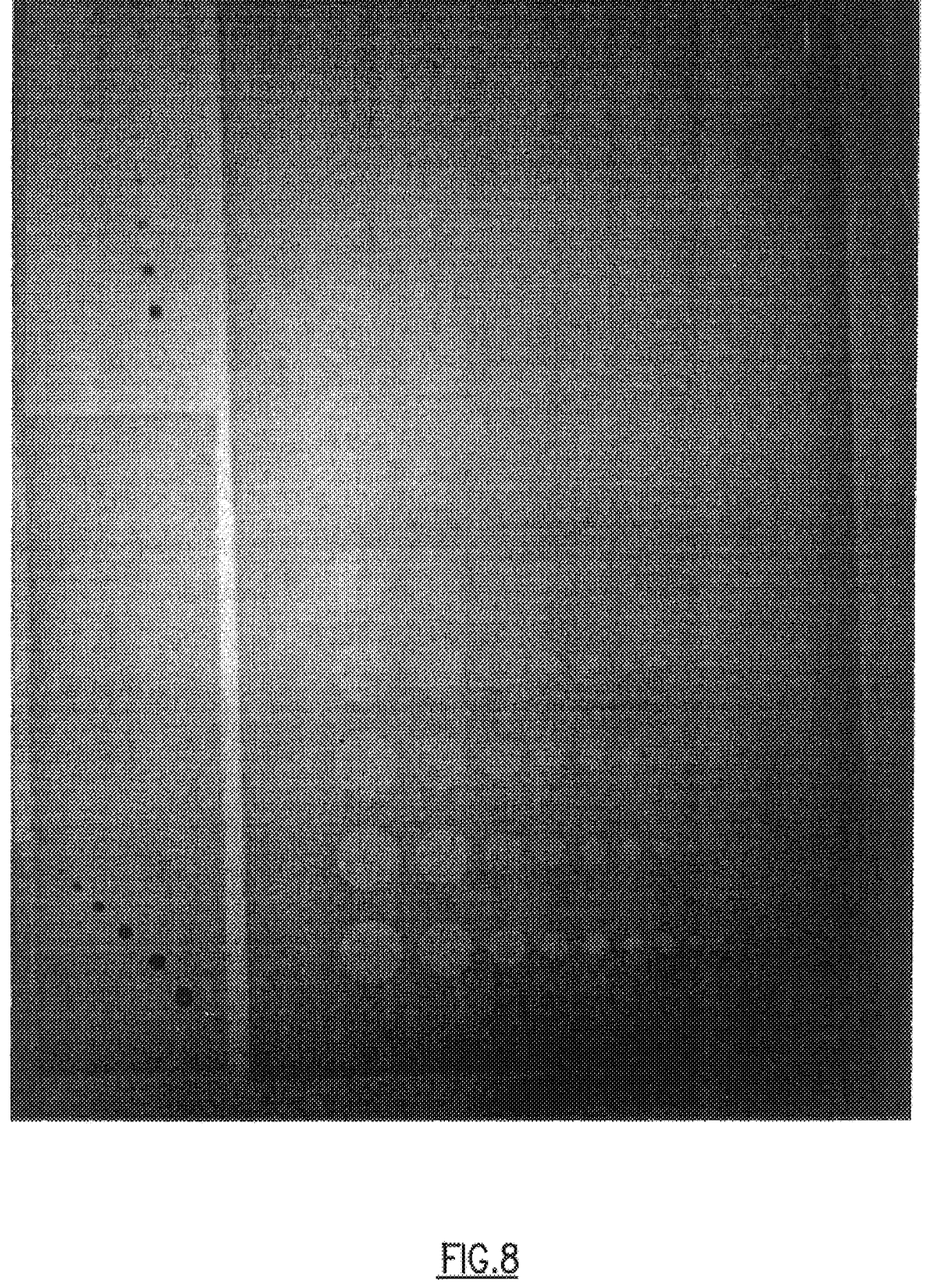
Figure 9:
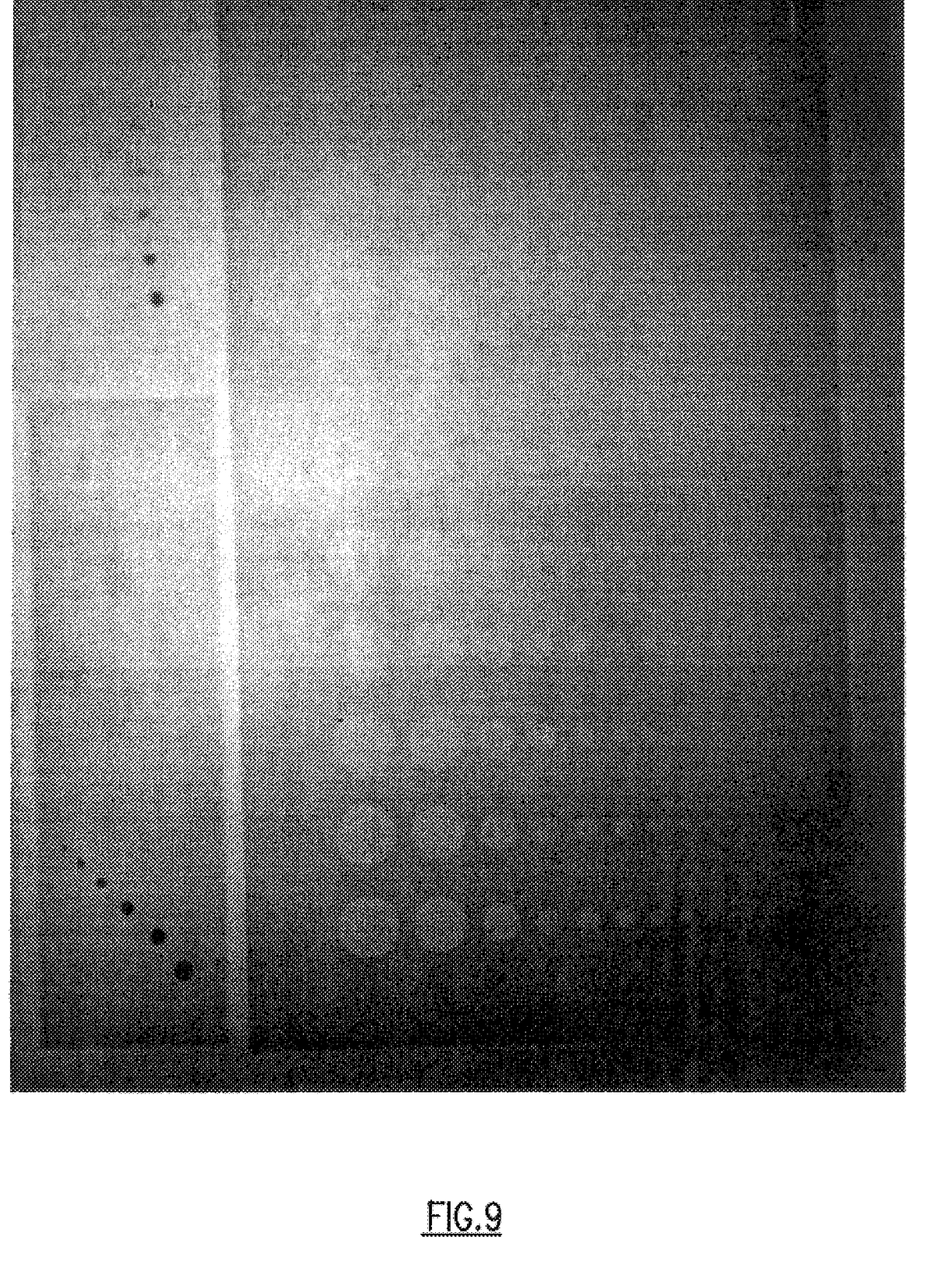

FIG. 8 illustrates a corresponding output image formed by taking the lowest ranking pixels of three successive images (MIN-3). This image has further improved resolution and contrast, and no discernible white spot noise. The process can be further refined, by taking the lowest ranking pixels from a greater number of successive images, e.g., the minimum value pixels of five images (MIN-5) as illustrated in FIG. 9. Here, however, there is little noticeable gain in resolution or contrast, and would not be necessary for many applications such as dental imaging or portal imaging.

It is also possible to select an intermediate ranking pixel value, such as the middle value of three images, for an appropriate application.

As mentioned above, the image can be acquired by any suitable means, not limited to the examples given here. Also, in addition to therapeutic, medical diagnostic, or dental imaging, there are many suitable industrial applications including x-ray or gamma-ray imaging of pipe welds or of stressed machine parts.

While the invention has been described with reference to certain preferred embodiments, it should be recognized that the invention is not limited to those precise embodiments. Rather, many modifications and variations would present themselves to persons skilled in the art without departing from the scope and spirit of the invention, as defined in the appended claims.

We claim:

1. Process for obtaining an x-ray generated video image and filtering the video image to remove x-ray-induced noise and scintillations and improve image quality, the process comprising:

obtaining said video image as a sequence of successive substantially identical images in registry with one another of an object irradiated with x-ray radiation, each said image being formed as an array of pixels each assigned to a respective pixel location and each pixel having a brightness value in a range from low to high;

for each respective pixel location, comparing the brightness values of the pixels of the respective images in rank order from low to high;

for each respective pixel location selecting one of the pixel values based on its rank order;

assembling the selected pixel values into an array of pixels to produce an output video image; and displaying said output video image.

2. The process of obtaining and filtering a video image according to claim 1, wherein said sequence of images comprises two successive images, and said selected pixel values are those of lower rank order.

3. The process of obtaining and filtering a video signal according to claim 1, wherein said sequence of images comprises three successive images, and said selected pixel values are those of lowest rank order.

4. The process of obtaining and filtering a video image according to claim 1, wherein said sequence of images comprises at least three images, and said selected pixel values are those of a selected intermediate rank.

5. Process of filtering from a radiological image spots resulting from isolated high levels of signal that occur as a result of undesired direct interaction of x-rays or gamma rays with an imaging medium which degrade the desired image that results from visible light from a scintillator struck by x-rays, the process comprising:

obtaining a sequence of successive substantially identical radiological images, in registry with one another, of an object, each said image being composed of an array of pixels each assigned to a respective pixel location and each pixel having a brightness value in a range from low to high;

for each respective pixel location, considering the brightness values of the pixels of the respective images in rank order from low to high;

for each respective pixel location selecting one of the pixel values based on its rank order;

assembling the selected pixel values into an array of pixels to produce an output video image; and displaying said output video image.

6. The process of claim 5 wherein the step of obtaining the images includes acquiring and storing a plurality of said successive images in respective memory locations, and said considering the brightness values includes comparing the pixel value for each stored image at each successive pixel location.

7. The process of claim 5 wherein the step of obtaining a sequence of images includes acquiring a first of said successive images and storing same as respective pixel values in a memory device having memory locations for the respective pixel locations thereof, and then acquiring at least a second successive image; as the second image is incoming comparing the pixel value of the incoming second image pixels with the stored pixel values in said memory device, and storing the lesser of the incoming and stored respective pixel value at each said memory location.

* * * * *

UNITED STATES PATENT AND TRADEMARK OFFICE
CERTIFICATE OF CORRECTION

PATENT NO. : 5,818,900

DATED : October 6, 1998

INVENTOR(S) : Thomas Vogelsong et al.

It is certified that error appears in the above-identified patent and that said Letters Patent is hereby corrected as shown below:

On the title page item [73], --

InfiMed, Inc., Liverpool, NY

Arizona Board of Regents on behalf of the University of Arizona, Tucson, AZ --.

Signed and Sealed this

Seventeenth Day of August, 1999

Attest:

Q. TODD DICKINSON

*Attesting Officer*       *Acting Commissioner of Patents and Trademarks*